United States Patent
> Iaquaniello et al.

(10) Patent No.: US 10,196,348 B2
(45) Date of Patent: Feb. 5, 2019

(54) METHOD FOR REVAMPING A UREA PRODUCTION COMPLEX

(71) Applicant: STAMICARBON B.V. ACTING UNDER THE NAME OF MT INNOVATION CENTER, Sittard (NL)

(72) Inventors: Gaetano Iaquaniello, Rome (IT); Joey Dobree, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 15/325,050

(22) PCT Filed: Apr. 21, 2015

(86) PCT No.: PCT/NL2015/050262
§ 371 (c)(1),
(2) Date: Jan. 9, 2017

(87) PCT Pub. No.: WO2016/010416
PCT Pub. Date: Jan. 21, 2016

(65) Prior Publication Data
US 2017/0166518 A1    Jun. 15, 2017

(30) Foreign Application Priority Data

Jul. 15, 2014   (EP) .................................. 14177054

(51) Int. Cl.
| C07C 273/04 | (2006.01) |
| C01B 3/48 | (2006.01) |
| C01B 3/38 | (2006.01) |
| B01J 19/24 | (2006.01) |
| C01C 1/04 | (2006.01) |
| C01B 32/50 | (2017.01) |

(52) U.S. Cl.
CPC ........... *C07C 273/04* (2013.01); *B01J 19/245* (2013.01); *C01B 3/382* (2013.01); *C01B 3/386* (2013.01); *C01B 3/48* (2013.01); *C01B 32/50* (2017.08); *C01C 1/0405* (2013.01); *C01C 1/0417* (2013.01); *C01C 1/0488* (2013.01); *B01J 2219/00024* (2013.01); *B01J 2219/24* (2013.01); *C01B 2203/0261* (2013.01); *C01B 2203/0283* (2013.01); *C01B 2203/0415* (2013.01); *C01B 2203/0475* (2013.01); *C01B 2203/068* (2013.01); *C01B 2203/1235* (2013.01); *C01B 2203/1241* (2013.01); *C01B 2203/141* (2013.01)

(58) Field of Classification Search
None
See application file for complete search history.

(56) References Cited

U.S. PATENT DOCUMENTS

| 6,448,441 B1 | 9/2002 | Wing-Chiu et al. | |
| 2014/0170052 A1* | 6/2014 | Iaquaniello | C01B 3/025 423/359 |
| 2014/0275626 A1* | 9/2014 | Iijima | C07C 273/04 564/67 |
| 2015/0031916 A1* | 1/2015 | Kiss | C07C 273/10 564/69 |

FOREIGN PATENT DOCUMENTS

WO    WO-2012/177137    12/2012

OTHER PUBLICATIONS

International Search Report for PCT/NL2015/050262, dated Jul. 13, 2015, 3 pages.

* cited by examiner

*Primary Examiner* — Clinton A Brooks
(74) *Attorney, Agent, or Firm* — Morrison & Foerster LLP

(57) ABSTRACT

The present invention provides a method for increasing the capacity of a urea production complex, the method comprising a step of adding to an existing urea production complex a $CO_2$ production unit, which unit employs a $CO_2$ production method comprising: i) subjecting a hydrocarbon feed to short contact time catalytic partial oxidation (SCT-CPO) to produce a first gas mixture comprising $H_2$, CO and $CO_2$, ii) subjecting said first gas mixture to a water gas shift reaction yielding a second gas mixture, iii) separating $CO_2$ from said second gas mixture yielding a purified $CO_2$ stream and a hydrogen containing stream and subsequently iv) reacting said purified $CO_2$ stream with ammonia from the ammonia production unit to produce urea. The invention also provides a urea production complex realized by the application of this method and a urea production method.

12 Claims, 1 Drawing Sheet

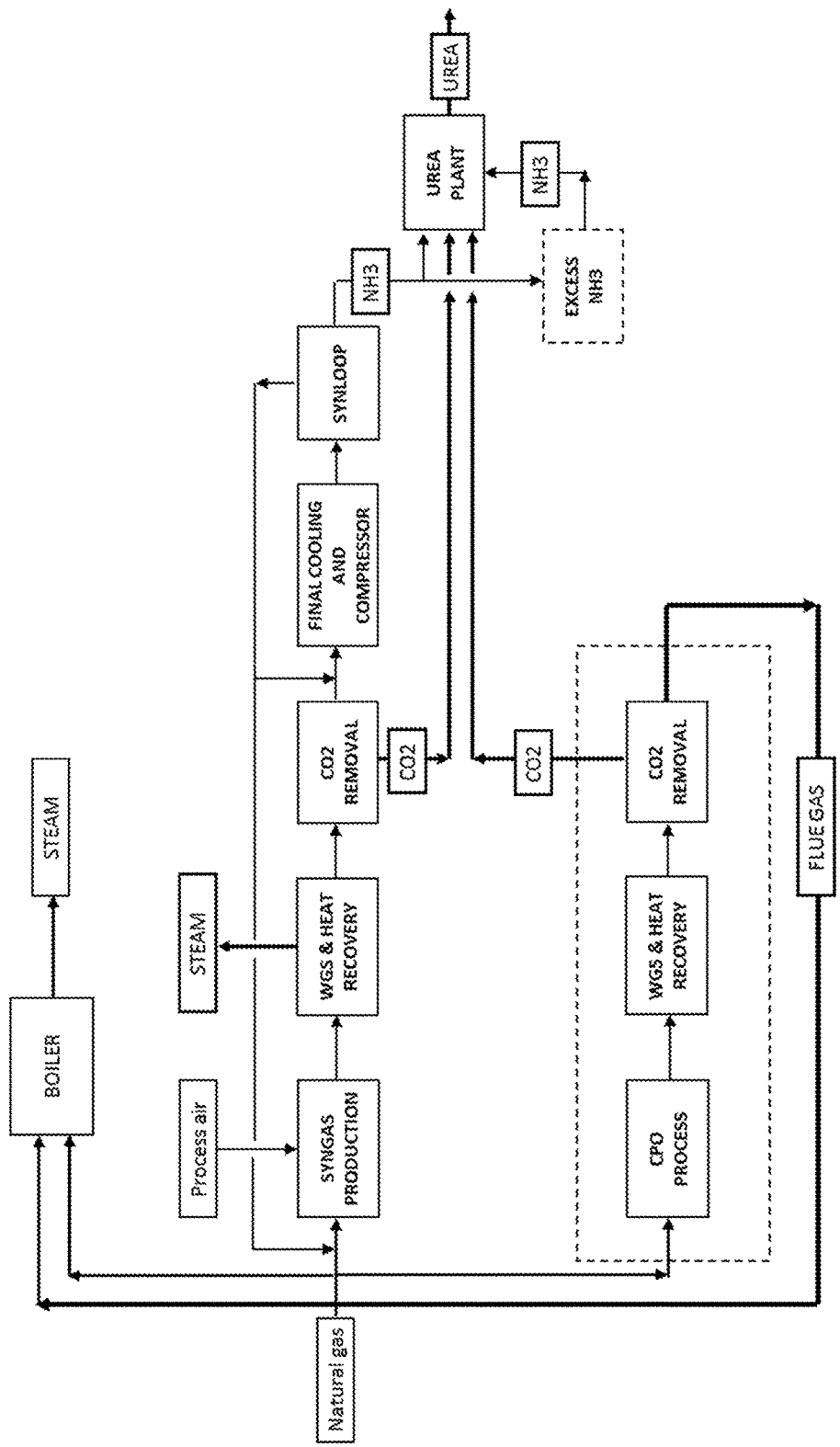

METHOD FOR REVAMPING A UREA PRODUCTION COMPLEX

CROSS-REFERENCE TO RELATED APPLICATIONS

This application is the national phase of PCT application PCT/NL2015/050262 having an international filing date of 21 Apr. 2015, which claims benefit of European patent application No. 14177054.5 filed 15 Jul. 2014. The contents of the above patent applications are incorporated by reference herein in their entirety.

FIELD OF THE INVENTION

The invention relates to the field of urea production and particularly discloses a method for increasing the capacity of a urea production complex by additional production of $CO_2$. The invention also discloses a urea production complex realized by the application of this method and a urea production method.

BACKGROUND OF THE INVENTION

A typical complex for urea production includes a syngas/hydrogen production plant, an ammonia production plant and a urea production plant. In a typical complex these plants are built as separate production units. The technologies used in the plants are often provided by different technology providers and design of each of their facilities is usually based on the specification at the battery limit of the previous plant.

The syngas/hydrogen production plant is often based on the conventional steam reforming (SR) process wherein natural gas is reacted with steam to form synthesis gas ($H_2+CO/CO_2$). The steam reforming process is endothermic and therefore additional natural gas is combusted in the burners in the reforming unit. The hydrogen is converted with nitrogen into ammonia in the ammonia production unit, while the $CO_2$ is used to react with the ammonia in the urea production unit.

A typical feature of this set up is that the overall process results in a stoichiometric excess of ammonia and consequently a shortage of $CO_2$. This excess of ammonia is typically sold, but this can lead to regulatory and safety issues related to ammonia transportation. Plant owners who desire or are required to consume the excess ammonia on site or wish to expand the capacity of an existing urea plant need to produce additional $CO_2$ to make up of the shortage. In a method known in the art additional $CO_2$ is recovered from flue gas by absorption in a solution, for example an amine solution. Flue gas of the steam reformer burners or flue gas of the auxiliary boiler which produces the steam required for the urea process can be used.

Disadvantages of this known method are that the volume of flue gas to be treated is high while the pressure thereof is typically atmospheric with a low partial pressure of $CO_2$ which leads to large equipment and consequent high capital costs and a need for a significant footprint nearby the steam reformer equipment. The presence of oxygen in the flue gas leads to degradation of the used solution which increases both raw material costs and the cost of disposing of the spent amine solution. Prior to entering the absorption tower, the flue gas needs to be cooled which requires additional equipment and the need for additional cooling water. The pressure drop created by the installation of the absorption system requires also an increase in the internal diameter of the exhaust fan, which may require replacement of the fan which increases both investment and operating cost.

It is therefore desired to provide a method to revamp urea plants by additionally producing $CO_2$, which method does not have the above disadvantages. Particularly, it is desired that this method is economical and does not require large additional equipment or high capital costs.

SUMMARY OF THE INVENTION

In order to better address one or more of the foregoing desires, the invention presents, in one aspect, a method for increasing the capacity of a urea production complex, the method comprising the steps of:

(a) providing an existing urea complex, said urea complex comprising a syngas production unit, an ammonia production unit and a urea production unit, which units produce respectively syngas, ammonia and urea, (b) adding to said existing urea production complex a $CO_2$ production unit, employing a $CO_2$ production method comprising:

i) subjecting a hydrocarbon feed to short contact time catalytic partial oxidation (SCT-CPO) to produce a first gas mixture comprising $H_2$, CO and $CO_2$, ii) subjecting said first gas mixture to a water gas shift reaction yielding a second gas mixture, iii) separating $CO_2$ from said second gas mixture yielding a purified $CO_2$ stream and a hydrogen containing stream, and iv) reacting said purified $CO_2$ stream with ammonia from the ammonia production unit to produce urea in the urea production unit.

In another aspect, the present invention provides a urea production complex comprising a syngas production unit wherein syngas is produced, an ammonia production unit wherein ammonia is produced, and a urea production unit wherein urea is produced, the complex further comprising a $CO_2$ production unit comprising:

a SCT-CPO reactor provided with an inlet for a hydrocarbon feed, an inlet for an oxygen containing feed and an outlet for a first gas mixture, a water gas shift reactor provided with an inlet for the first gas mixture and an outlet for a second gas mixture, a $CO_2$ removal unit, provided with an inlet for the second gas mixture, an outlet for a $CO_2$ stream and an outlet for a hydrogen containing stream, wherein $CO_2$ is separated from the second gas mixture, wherein the $CO_2$ removal unit is connected with the urea production unit so that the $CO_2$ stream obtained in the $CO_2$ removal unit is used as a $CO_2$ feed for urea production.

In a further aspect, the present invention provides a method for urea production from an ammonia feed and a carbon dioxide feed, wherein at least part of the carbon dioxide feed is obtained employing a $CO_2$ production method comprising:

i) subjecting a hydrocarbon feed to short contact time catalytic partial oxidation (SCT-CPO) to produce a first gas mixture comprising $H_2$, CO and $CO_2$, ii) subjecting said first gas mixture to a water gas shift reaction yielding a second gas mixture, iii) separating $CO_2$ from said second gas mixture yielding a purified $CO_2$ stream and a hydrogen containing stream.

DETAILED DESCRIPTION OF THE INVENTION

The invention provides a method to increase the capacity of an existing urea production complex, which involves an additional $CO_2$ production on site to compensate for the mismatch in the production between ammonia and $CO_2$. The method according to the invention comprises several steps.

In a first step, step (a), an existing urea complex is provided, said urea complex comprising a syngas production unit, an ammonia production unit and a urea production unit. Generally, in the syngas production unit a hydrocarbon feed, such as natural gas, is subjected to steam reforming to produce a syngas mixture, mainly comprising CO and $H_2$. In a preferred embodiment, steam reforming is used to produce syngas, since the combination of syngas production by steam reforming and additional $CO_2$ production by SCT-CPO is particularly beneficial for the effect of optimized $CO_2$ production. Alternatively or in addition to steam reforming, autothermal reforming can be used to produce syngas. In some embodiments, it is preferred to use steam reforming coupled to autothermal reforming to produce syngas. In the ammonia production unit, hydrogen and nitrogen are reacted to produce ammonia, which in turn is supplied to the urea production unit, wherein urea is produced. The above processes and equipment are known to a skilled person. The urea production unit preferably operates according to a stripping urea process, but any urea production process can be used.

In a second step, step (b), a $CO_2$ production unit is added to the existing urea production complex that generates additional $CO_2$. The $CO_2$ production method employed in the $CO_2$ production unit comprises the following steps:

i) subjecting a hydrocarbon feed, for example natural gas, to short contact time catalytic partial oxidation (SCT-CPO) to produce a first gas mixture comprising $H_2$, CO and $CO_2$, ii) subjecting said first gas mixture to a water gas shift (WGS) reaction yielding a second gas mixture, iii) separating $CO_2$ from said second gas mixture yielding a purified $CO_2$ stream and a hydrogen containing stream and subsequently iv) reacting said purified $CO_2$ stream with ammonia from the ammonia production unit to produce urea in the urea production unit.

In step (i), the hydrocarbon feed is fed together with air (or other source of oxygen) into a CPO reactor, wherein syngas is produced. Any hydrocarbon containing feed suitable for catalytic partial oxidation can be used. Under hydrocarbon feed any feed containing at least one hydrocarbon is meant. It is preferred that the hydrocarbons used for the SCT-CPO are in the gaseous or liquid state at ambient conditions. Preferably, the feed contains light hydrocarbons such as $C_{1-4}$ alkanes, e.g. methane, ethane, etc. More preferably, the feed contains methane or a gas containing substantial amounts of methane, e.g. natural gas or synthetic (from coal). It is preferred to use a desulfurized feed. Therefore, if needed, the hydrocarbon feed can be subjected to a desulfurization step prior to the SCT-CPO.

As an oxygen source in SCT-CPO, preferably air or oxygen enriched air is used. Oxygen enriched air may be used if the cost of the oxygen is low. This allows the unit to be smaller. One of the advantages of the described process, however, is that air can be used so there is no need to add an (expensive) air separation unit (ASU) to produce oxygen. This is not conventionally done as in most CPO units preferably enriched air or oxygen is used. This is because it obviates the need to separate $N_2$ from the syngas which is expensive. In the present invention, however, $N_2$ may be present in a mixture with syngas and this does not affect the further process, which is an important advantage of the present process. The use of air allows to avoid the costs needed for using ASU to produce oxygen. Therefore, in a preferred embodiment the SCT-CPO is performed in the presence of air as the oxygen source.

The term short contact time catalytic partial oxidation (SCT-CPO) is known to the skilled person. The CPO reaction takes place in a reactor under the influence of a catalyst at residence times between $10^{-2}$ to $10^{-4}$ and with typical catalyst surface contact times around $10^{-6}$ s$^{-1}$. These contact time correspond to typical space velocities of 100,000 to 250,000 hr$^{-1}$, preferably 100,000 to 200,000 hr$^{-1}$. Catalysts employed for SCT-CPO comprise Ni, Pd, Pt, Rh, or Ru. The reaction takes place at catalyst surface temperatures above 950° C., preferably above 1000° C. By employing said short contact times and high catalyst surface temperatures the formation of CO is highly favoured and the formation of carbon or $CO_2$ is suppressed. This leads to a highly favourable synthesis gas composition. A reference to CPO is (a) L. Basini, Catalysis Today 117 (2006) 384-393. Other references include (b) L. Basini, K. Aasberg-Petersen, A. Guarinoni, M. Oestberg, Catalysis Today (2001) 64, 9-20 "Catalytic Partial Oxidation of Natural Gas at Elevated Pressure and Low Residence Time"; (c) H. Hickman, L. D. Schmidt, J. Catal. 138 (1992) 267; (d) D. Hichman, L. D. Schmidt Science, 259 (1993) 343; (e) L. Basini, G. Donati WO 97/37929; (f) Sanfilippo, Domenico; Basini, Luca; Marchionna, Mario; EP-640559; (g) D. Schaddenhorst, R. J. Schoonebeek; WO 00/00426; (h) K. L. Hohn, L. D. Schmidt, S. Reyes, J. S. Freeley, WO 01/32556; (i) A. M. Gaffney, R. Songer, R. Ostwald, D. Corbin, WO 01/36323.

In a preferred embodiment, the capacity of the SCT-CPO process in terms of $CO_2$ production is less than 20%, and preferably less than 15%, of the $CO_2$ production by the steam reformer. That is, the amount of $CO_2$ produced by the CPO unit is lower than the amount of $CO_2$ produced by the steam reforming. This means a relatively small size of the CPO equipment, which can then be easier placed near the urea synthesis section. There is no need to install this near the steam reformer. The CPO and other equipment can be added as a completely separate unit for example as a skid mounted unit.

The obtained first gas mixture may be cooled prior to step (ii). In one embodiment, the first gas mixture is cooled by quenching with water. The quench water is preferably taken from a condensed steam stream or a process condensate stream from the urea production unit. In another embodiment, the first gas mixture is cooled by indirect heat exchange in a heat exchanger, e.g. a waste heat boiler, wherein the cooling medium provided to the heat exchanger is boiler feed water (BFW) from the urea production unit. Preferably, the BFW is raised in pressure to obtain steam with high pressure (such as 12 to 22 bar) and is subsequently used in the urea synthesis, for example in the high pressure stripper of the urea production unit.

In step (ii), the first gas mixture obtained in the SCT-CPO step is subjected to a water gas shift (WGS) reaction. This can suitably take place in a WGS reactor. During the WGS reaction, the available CO is converted to $CO_2$ in the presence of steam reducing thereby the $CO/CO_2$ ratio of the first gas mixture. As a result of the WGS reaction, a second gas mixture is obtained, which contains mainly carbon dioxide and hydrogen.

In step (iii), $CO_2$ is separated from the second gas mixture yielding a purified $CO_2$ stream and a hydrogen containing stream. Under "separated" it is understood that a particular component of the mixture is separated in a substantially pure form. A process for separating $CO_2$, wherein $CO_2$ is a component in a mixture, is a process which acts on $CO_2$ to separate it from the mixture. When air is used in the SCT-CPO as the source of oxygen, the resulting gas mixture is mostly a three component mixture, containing $H_2$, $CO_2$, $N_2$, possible with traces of CO. In the separation step, this mixture is divided into a purified $CO_2$ stream, which substantially contains $CO_2$, and a hydrogen containing stream that may contain other components and impurities. Substantially in this case means a purity of at least 95 vol. %, preferably at least 98 vol. %, for example at least 99 vol. % $CO_2$.

The purified $CO_2$ stream can be obtained from the second gas mixture by different methods. Preferably, it is obtained by an absorption process. More preferably, the absorption process is selected from an amine absorption process or a chilled ammonia process. In an amine absorption process, a carbon dioxide containing gas mixture is brought in contact with an amine solution in an absorption column, whereby the $CO_2$ binds to the amine and is thereby removed from the gas mixture. The capture of $CO_2$ from the syngas is preferably done at high pressure. In a second step, the amine is regenerated by heating the solution to expel the $CO_2$. The advantage of these methods is that a high purity $CO_2$ stream suitable for urea production is obtained, which can be directly used in the urea production unit. In the embodiment wherein the $CO_2$ production unit is completely separated from the existing ammonia production unit there is an additional advantage that there is no need to increase the exhaust fan power.

Separating $CO_2$ from the second gas mixture does not have the disadvantages of the separation of $CO_2$ from the flue gas originating from the burners of the steam reformer or of auxiliary burners in the ammonia or urea production units. The use of the flue gas as a source of additional $CO_2$ is generally very costly. First of all, the $CO_2$ partial pressure in the flue gas is low. At about atmospheric pressure the flue gas is usually available with a $CO_2$ concentration in the range of 8-13 vol. %. The required pressure drop in the system is also low, to avoid too high compression costs of flue gases. There is also a need to cool the flue gas to about ambient temperature, which requires to add a specific column for such duty and reject all the extracted heat as cooling water. Further, the regeneration duty for the selected solvent as result of the low pressure operation is relatively high. Importantly, the presence of oxygen in the flue gases together with $NO_x$ and $SO_x$ increases solvent degradation and presence of corrosive by-products. In fact, sulphur containing components are harmful for the hydrogen convertor catalyst and lead to corrosion of the urea synthesis process. This will increase not only the cost of solvent per ton of $CO_2$ captured, but also the need to dispose the by-products generated by the solvent degradation in a proper way. Consequently, the process based on separating additional $CO_2$ from the flue gases is not economical.

In contrast to the above disadvantages, the present invention provides an economical process of increasing the capacity of a urea complex, wherein additional $CO_2$ is produced using the SCT-CPO and WGS processes. Particularly, the separation of $CO_2$ from the gas mixture resulting from WGS is much more efficient than from flue gases because of a higher $CO_2$ partial pressure in the mixture, higher total pressure of the mixture, a lower temperature of the mixture and consequently less need to cool it before the separation step.

The remaining hydrogen containing stream can be used elsewhere in the urea production complex. Preferably, it is used as fuel in an auxiliary boiler which produces the steam required for the ammonia or urea process, or in the burners of the steam reformer. This gas stream mainly contains hydrogen, nitrogen (if air is used in the SCT-CPO step), $CH_4$ and CO.

In step (iv), the purified $CO_2$ stream is reacted with ammonia from the ammonia production unit to produce urea in the urea production unit.

In one embodiment, the purified $CO_2$ stream is fed to the urea production unit in the existing $CO_2$ compressor which compresses $CO_2$ for use in the urea high pressure synthesis. Typical pressures are 10 to 20 MPa (100-200 bar). This embodiment requires that the $CO_2$ separation capacity of the existing ammonia plant is sufficient.

In another embodiment, typically when the capacity of the $CO_2$ compressor in the high pressure section is insufficient, the second gas mixture can be sent to a newly installed (small) $CO_2$ separation unit, which provides the purified $CO_2$ stream. This stream is then compressed to medium pressure (1-7 MPa) in an additional (small) $CO_2$ compressor and fed to a medium pressure synthesis section of the urea production unit. In one such embodiment the medium pressure synthesis section comprises a medium pressure stripper and the $CO_2$ is employed as stripping gas in the medium pressure stripper.

In yet another aspect, the present invention provides a urea production complex with increased capacity which is realized by applying the method according to the present invention.

Such urea production complex comprises a syngas production unit wherein syngas is produced, an ammonia production unit wherein ammonia is produced, and a urea production unit wherein urea is produced, the complex further comprising a $CO_2$ production unit comprising:

a SCT-CPO reactor provided with an inlet for a hydrocarbon feed, an inlet for an oxygen containing feed and an outlet for a first gas mixture, a water gas shift reactor provided with an inlet for the first gas mixture and an outlet for a second gas mixture, a $CO_2$ removal unit, provided with an inlet for the second gas mixture, an outlet for a $CO_2$ stream and an outlet for a hydrogen containing stream, wherein $CO_2$ is separated from the second gas mixture, wherein the $CO_2$ removal unit is connected with the urea production unit so that the $CO_2$ stream obtained in the $CO_2$ removal unit is used as a $CO_2$ feed for urea production.

In a preferred embodiment, the $CO_2$ removal unit is connected with the urea production unit. Preferably, the outlet for the hydrogen containing stream of the $CO_2$ removal unit is connected with a burner of the steam reformer and/or a burner present elsewhere in the urea production complex. For example, with the steam reformer in the syngas production unit, or with auxiliary burners used for steam production in the ammonia or urea production unit.

In one embodiment, the purified $CO_2$ stream from the $CO_2$ removal unit is connected with the $CO_2$ compressor which compresses $CO_2$ for use in the urea high pressure synthesis in the urea production unit. Typical pressure are 10 to 20 MPa (100-200 bar). This embodiment requires that the $CO_2$ separation capacity of the existing ammonia plant is sufficient.

In another embodiment, typically when the capacity of the $CO_2$ compressor in the high pressure section is insufficient, the second gas mixture can be sent to a newly installed (small) $CO_2$ separation unit, which provides the purified $CO_2$ stream. This stream is then compressed to medium pressure (1-7 MPa) in an additional (small) $CO_2$ compressor and fed to a medium pressure synthesis section of the urea production unit.

In yet a further aspect, the invention provides a method for urea production that can be realized in the urea production complex according to the invention. The method allows to produce urea from an ammonia feed and a carbon dioxide feed, wherein at least part of the carbon dioxide feed is obtained employing a $CO_2$ production method comprising:

i) subjecting a hydrocarbon feed to short contact time catalytic partial oxidation (SCT-CPO) to produce a first gas mixture comprising $H_2$, CO and $CO_2$, ii) subjecting said first gas mixture to a water gas shift reaction yielding a second gas mixture, iii) separating $CO_2$ from said second gas mixture yielding a purified $CO_2$ stream and a hydrogen containing stream. Preferably, only part of the carbon dioxide feed is obtained according the described $CO_2$ production method.

Typically, the ammonia feed is produced (at least, in part) in an ammonia production unit from hydrogen and nitrogen. Hydrogen used for the ammonia synthesis is preferably obtained from a syngas produced in the syngas production unit. In a preferred embodiment, the syngas production unit performs steam reforming of a hydrocarbon feed. The hydrocarbon feed used for the syngas production can be the same as or different from the feed used for the $CO_2$ production in the $CO_2$ production unit. Steam reforming also produces $CO_2$ that is preferably used as part of the $CO_2$ feed for the urea production, together with the additionally produced $CO_2$ in the $CO_2$ production unit.

An embodiment according to the invention is illustrated in FIG. 1. This FIGURE schematically shows a process of urea production that is modified by adding a $CO_2$ production unit.

Natural gas is supplied to a syngas production unit, wherein it is reacted with process air (by steam reforming and/or autothermal reforming) to produce a syngas mixture. The syngas is then subjected to a water gas shift reaction and heat recovery, whereby steam is generated that can be used elsewhere in the process. The mixture obtained in the WGS reaction is subjected to $CO_2$ removal and the separated $CO_2$ is sent to the urea plant. The remaining mixture containing hydrogen is cooled and compressed and used in the synthesis loop to produce ammonia in an ammonia production unit. The produced ammonia is then sent to the urea plant for urea synthesis.

Additional $CO_2$ is produced in an add-on process depicted in the lower part of the FIGURE. Natural gas is subjected to SCT-CPO to produce a first gas mixture comprising hydrogen, CO and $CO_2$, which mixture is subjected to WGS reaction yielding a second gas mixture. From the second gas mixture $CO_2$ is removed to obtain a purified $CO_2$ stream sent to the urea plant, and a hydrogen containing flue gas. The hydrogen containing flue gas is sent as part of the fuel to an auxiliary boiler, which produces steam that can be used, e.g. in the ammonia or urea process (not shown).

The invention claimed is:

1. A method for obtaining an improved urea production complex with increased capacity compared to an existing urea complex, the method comprising the steps of:
 (a) providing an existing urea complex, said urea complex comprising a syngas production unit, an ammonia production unit and a urea production unit, which units produce respectively syngas, ammonia and urea, wherein said syngas production unit is a steam reformer and/or an autothermal reformer,
 wherein said ammonia production unit is configured to produce said ammonia at least partially by a method comprising reacting nitrogen with hydrogen obtained from syngas produced in said syngas production unit,
 (b) adding to said existing urea production complex a $CO_2$ production unit, wherein the $CO_2$ production unit comprises:
 (i) a short contact time catalytic partial oxidation reactor (SCT-CPO reactor) provided with an inlet for a hydrocarbon feed, an inlet for an oxygen containing feed and an outlet for a first gas mixture,
 (ii) a water gas shift (WGS) reactor provided with an inlet for the first gas mixture and an outlet for a second gas mixture, and
 (iii) a $CO_2$ removal unit, provided with an inlet for the second gas mixture, an outlet for a purified $CO_2$ stream and an outlet for a hydrogen containing stream, wherein $CO_2$ is separated from the second gas mixture, and wherein the $CO_2$ removal unit is connected with the urea production unit so that the purified $CO_2$ stream obtained in the $CO_2$ removal unit is used as a $CO_2$ feed for urea production,
 so as to obtain an improved urea production complex.

2. The method according to claim 1, wherein said syngas production unit of said existing urea complex is a steam reforming unit with natural gas supply to said steam reforming unit.

3. The method according to claim 2, wherein the capacity of the SCT-CPO in terms of $CO_2$ production is less than 20% of the $CO_2$ production capacity of the steam reforming unit.

4. A method for urea production from an ammonia feed and a carbon dioxide feed, wherein at least a portion of the carbon dioxide feed is produced by a method comprising:
 i) subjecting a hydrocarbon feed to short contact time catalytic partial oxidation (SCT-CPO) to produce a first gas mixture comprising $H_2$, CO and $CO_2$,
 ii) subjecting said first gas mixture to a water gas shift reaction yielding a second gas mixture,
 iii) separating $CO_2$ from said second gas mixture yielding a purified $CO_2$ stream and a hydrogen containing stream, and
 iv) reacting $CO_2$ obtained in step (iii) with ammonia feed to form urea in a urea production unit which includes a syngas production unit; and
 wherein said ammonia feed is at least partially produced by a method comprising reacting nitrogen with hydrogen wherein said hydrogen is produced by steam reforming and/or autothermal reforming.

5. The method of claim 4, wherein said hydrogen containing stream is used as fuel in an auxiliary boiler, which produces steam required for the ammonia or urea synthesis, or in the syngas production unit of the urea production unit.

6. The method of claim 4, wherein the first gas mixture is cooled by quenching with water prior to the water gas shift reaction.

7. The method of claim 6, wherein the quench water is taken from a condensed steam stream or a process condensate stream from the urea production unit.

8. The method of claim 4, wherein the first gas mixture is cooled by indirect heat exchange in a heat exchanger wherein the cooling medium provided to the heat exchanger is boiler feed water (BFW) from the urea production unit.

9. The method of claim 8, wherein during the indirect heat exchange the boiler feed water is raised in pressure to produce steam with a pressure 12-22 bar and is subsequently used in the urea synthesis.

10. The method of claim 4, wherein the SCT-CPO is performed in the presence of air as the oxygen source.

11. The method of claim 4, wherein the purified $CO_2$ stream is fed to the $CO_2$ compressor of the urea production unit, which compresses $CO_2$ for use in the high pressure synthesis section of the urea production unit.

12. The method of claim 4, wherein the purified $CO_2$ stream is compressed to medium pressure and fed to a medium pressure synthesis section of the urea production unit.

* * * * *